(12) United States Patent
Tang et al.

(10) Patent No.: US 11,638,612 B2
(45) Date of Patent: May 2, 2023

(54) AUTOMATIC ABLATION ANTENNA SEGMENTATION FROM CT IMAGE

(71) Applicant: Covidien LP, Mansfield, MA (US)

(72) Inventors: Qi Tang, Shanghai (CN); Darren G. Girotto, Louisville, CO (US); Jianxin Ou, Shanghai (CN)

(73) Assignee: Covidien LP, Mansfield, MA (US)

( * ) Notice: Subject to any disclaimer, the term of this patent is extended or adjusted under 35 U.S.C. 154(b) by 286 days.

(21) Appl. No.: 16/769,677

(22) PCT Filed: Dec. 4, 2017

(86) PCT No.: PCT/CN2017/114461
§ 371 (c)(1),
(2) Date: Jun. 4, 2020

(87) PCT Pub. No.: WO2019/109211
PCT Pub. Date: Jun. 13, 2019

(65) Prior Publication Data
US 2020/0375664 A1    Dec. 3, 2020

(51) Int. Cl.
*A61B 34/20*  (2016.01)
*A61B 90/00*  (2016.01)
(Continued)

(52) U.S. Cl.
CPC .......... *A61B 34/20* (2016.02); *A61B 18/1815* (2013.01); *A61B 90/37* (2016.02);
(Continued)

(58) Field of Classification Search
CPC .......... G06T 7/0012; G06T 7/20; G06T 7/70; G06T 2207/20224; G06T 2207/30241; G06V 2201/034
See application file for complete search history.

(56) References Cited

U.S. PATENT DOCUMENTS

2005/0090742 A1   4/2005  Mine et al.
2008/0039715 A1   2/2008  Wilson et al.
(Continued)

FOREIGN PATENT DOCUMENTS

CN       101536013 A      9/2009
JP       2000102533 A     4/2000
(Continued)

OTHER PUBLICATIONS

Gavaghan et al. "An evaluation of image overlay projection guidance for liver tumour targeting." (2012). (Year: 2012).*
(Continued)

*Primary Examiner* — Katrina R Fujita
(74) *Attorney, Agent, or Firm* — Carter, DeLuca & Farrell LLP

(57) ABSTRACT

Provided in accordance with the present disclosure are systems and methods for identifying a percutaneous tool in image data. An exemplary method includes receiving image data of at least a portion of a patient's body, identifying an entry point of a percutaneous tool through the patient's skin in the image data, analyzing a portion of the image data including the entry point of the percutaneous tool through that patient's skin to identify a portion of the percutaneous tool inserted through the patient's skin, determining a trajectory of the percutaneous tool based on the identified portion of the percutaneous tool inserted through the patient's skin, identifying a remaining portion of the percutaneous tool in the image data based on the identified entry point and the determined trajectory of the percutaneous tool, and displaying the identified portions of the percutaneous tool on the image data.

20 Claims, 8 Drawing Sheets

(51) Int. Cl.
  *G06T 7/70* (2017.01)
  *A61B 18/18* (2006.01)
  *G06T 7/00* (2017.01)
  *G06T 7/20* (2017.01)
  *G06V 20/20* (2022.01)
  *A61B 18/00* (2006.01)

(52) U.S. Cl.
  CPC .............. *G06T 7/0012* (2013.01); *G06T 7/20* (2013.01); *G06T 7/70* (2017.01); *G06V 20/20* (2022.01); *A61B 2018/00577* (2013.01); *A61B 2018/1823* (2013.01); *A61B 2018/1869* (2013.01); *A61B 2034/2065* (2016.02); *A61B 2090/378* (2016.02); *A61B 2090/3762* (2016.02); *G06T 2207/20224* (2013.01); *G06T 2207/30241* (2013.01); *G06V 2201/034* (2022.01)

(56) References Cited

U.S. PATENT DOCUMENTS

| | | | |
|---|---|---|---|
| 2008/0221446 A1* | 9/2008 | Washburn | A61B 8/4254 600/437 |
| 2009/0274271 A1 | 11/2009 | Pfister et al. | |
| 2012/0004539 A1* | 1/2012 | Gardi | G06T 7/70 600/424 |
| 2012/0078103 A1 | 3/2012 | Tashiro et al. | |
| 2013/0151608 A1 | 6/2013 | Wiseman et al. | |
| 2013/0204124 A1* | 8/2013 | Duindam | A61B 5/062 604/272 |
| 2013/0316318 A1 | 11/2013 | Frank et al. | |
| 2014/0072099 A1 | 3/2014 | Mukumoto et al. | |
| 2015/0018670 A1 | 1/2015 | Hartkens et al. | |
| 2016/0317224 A1 | 11/2016 | Girotto et al. | |
| 2018/0318009 A1* | 11/2018 | Sohlden | A61B 90/96 |

FOREIGN PATENT DOCUMENTS

| | | |
|---|---|---|
| JP | 2001252286 A | 9/2001 |
| JP | 2005058584 A | 3/2005 |
| JP | 2007117734 A | 5/2007 |
| JP | 2012070837 A | 4/2012 |
| JP | 2013165756 A | 8/2013 |
| JP | 2013172951 A | 9/2013 |
| JP | 2015047303 A | 3/2015 |
| WO | 2008107874 A2 | 9/2008 |

OTHER PUBLICATIONS

Extended European Search Report issued in corresponding application EP 17934129.2 dated Jun. 5, 2021 (6 pages).
International Search Report issued in corresponding Appl. No. PCT/CN2017/114461 dated Jun. 28, 2018 (3 pages).
Written Opinion of the International Searching Authority issued in corresponding Appl. No. PCT/CN2017/114461 dated Jun. 28, 2018 (4 pages).
Japanese Office Action issued in corresponding application JP 2020-547262 dated Sep. 3, 2021, together with English language translation (9 pages).
Final Office Action issued in corresponding Japanese Application 2020-547262 dated Apr. 22, 2022, together with English language translation (6 pages).
Office Action issued in corresponding application JP 2020-547262 dated Mar. 16, 2023, together with English language translation retrieved from the Global Dossier (32 pages).

* cited by examiner

AUTOMATIC ABLATION ANTENNA SEGMENTATION FROM CT IMAGE

CROSS-REFERENCE TO RELATED APPLICATIONS

This application is a national stage of International Patent Application No. PCT/CN2017/114461, filed on Dec. 4, 2017.

BACKGROUND

Technical Field

The present disclosure relates to ablation antenna segmentation and, more particularly, to the systems, devices, and methods for automated identification and segmentation of an ablation antenna in a computed tomography image.

Description of Related Art

Computed tomography (CT) images are commonly used to identify objects, such physiological structures as well as medical instruments, in a patient's body. Various CT scans may be performed before and/or during a medical procedure to identify such objects and to monitor progress of the medical procedure. However, the objects may not always be detectable, in part or in whole, based solely on CT images. Further, interference with CT scans may be caused by various sources, and mitigation of such interference is not always possible. Described hereinbelow are improved systems, devices, and methods for identifying objects, and particularly medical instruments, in CT images.

SUMMARY

Provided in accordance with embodiments of the present disclosure is a method for identifying a percutaneous tool in image data. In an aspect of the present disclosure, an illustrative method includes receiving image data of at least a portion of a patient's body, identifying an entry point of a percutaneous tool through the patient's skin in the image data, analyzing a portion of the image data including the entry point of the percutaneous tool through that patient's skin to identify a portion of the percutaneous tool inserted through the patient's skin, determining a trajectory of the percutaneous tool based on the identified portion of the percutaneous tool inserted through the patient's skin, identifying a remaining portion of the percutaneous tool in the image data based on the identified entry point and the determined trajectory of the percutaneous tool, and displaying the identified portions of the percutaneous tool on the image data.

In another aspect of the present disclosure, the method further includes receiving characteristic data of the percutaneous tool, and identifying the remaining portion of the percutaneous tool in the image data is further based on the characteristic data of the percutaneous tool.

In a further aspect of the present disclosure, the characteristic data of the percutaneous tool includes one or more of a length of the percutaneous tool, a diameter of the percutaneous tool, and a flexibility metric of the percutaneous tool.

In another aspect of the present disclosure, determining a trajectory of the percutaneous tool based on the identified portion of the percutaneous tool inserted through the patient's skin includes determining an angle of insertion of the identified portion of the percutaneous tool inserted through the patient's skin, and determining a trajectory of the percutaneous tool based on the angle of insertion of the identified portion of the percutaneous tool inserted through the patient's skin.

In yet another aspect of the present disclosure, the method further includes identifying a target location in the image data, determining a path from the entry point to the target location, determining whether the trajectory of the percutaneous tool corresponds to the path, and displaying the identified portions of the percutaneous tool, the trajectory, and the path on the image data.

In a further aspect of the present disclosure, if it is determined that the trajectory of the percutaneous tool does not correspond to the path, the method further includes determining a difference between the trajectory and the path, and displaying guidance for adjusting an angle of the percutaneous tool based on the determined difference between the trajectory and the path.

In another aspect of the present disclosure, the percutaneous tool is an ablation needle, and the method further includes receiving configuration settings for an ablation procedure, identifying a position of a radiating portion of the percutaneous tool in the image data, determining a projected ablation zone based on the configuration settings and the identified position of the radiating portion of the percutaneous tool, and displaying the projected ablation zone on the image data.

In a further aspect of the present disclosure, the method further includes receiving an indication that the radiating portion of the percutaneous tool has been activated, determining a progress of an ablation procedure based on the configuration settings and a time during which the percutaneous tool has been activated, and displaying an estimated ablated zone based on the determined progress of the ablation procedure.

In another aspect of the present disclosure, the method further includes identifying a distal portion of the percutaneous tool in the image data, determining a line in the image data between the entry point and the distal portion of the percutaneous tool, and displaying the determined line on the image data.

In a further aspect of the present disclosure, the distal portion of the percutaneous tool is identified based on characteristic data of the percutaneous tool.

In yet a further aspect of the present disclosure, the distal portion of the percutaneous tool is identified based on an electromagnetic sensor included in the percutaneous tool.

In another aspect of the present disclosure, identifying the remaining portion of the percutaneous tool includes analyzing the image data to identify high intensity areas along the determined line, and including portions of the high intensity areas along a length of the determined line and within a radius of the determined line, and the radius is determined based on a diameter characteristic of the percutaneous tool.

In a further aspect of the present disclosure, identifying the remaining portion of the percutaneous tool further includes excluding portions of the high intensity areas along the length of the determined line and outside of the radius of the determined line.

Provided in accordance with embodiments of the present disclosure is a system for identifying a percutaneous tool in image data. In an aspect of the present disclosure, the system includes a percutaneous tool, a display device, and a computing device including a processor and a memory storing instructions which, when executed by the processor, cause the computing device to receive image data of at least a portion of a patient's body, identify an entry point of the percutaneous tool through the patient's skin in the image data, analyze a portion of the image data including the entry point of the percutaneous tool through that patient's skin to identify a portion of the percutaneous tool inserted through the patient's skin, determine a trajectory of the percutaneous tool based on the identified portion of the percutaneous tool inserted through the patient's skin, identify a remaining portion of the percutaneous tool in the image data based on the identified entry point and the determined trajectory of the percutaneous tool, and display the identified portions of the percutaneous tool on the image data.

Provided in accordance with embodiments of the present disclosure is a non-transitory computer-readable storage medium storing a program for identifying a percutaneous tool in image data. In an aspect of the present disclosure, the program includes instructions which, when executed by a processor, cause a computing device to receive image data of at least a portion of a patient's body, identify an entry point of the percutaneous tool through the patient's skin in the image data, analyze a portion of the image data including the entry point of the percutaneous tool through that patient's skin to identify a portion of the percutaneous tool inserted through the patient's skin, determine a trajectory of the percutaneous tool based on the identified portion of the percutaneous tool inserted through the patient's skin, identify a remaining portion of the percutaneous tool in the image data based on the identified entry point and the determined trajectory of the percutaneous tool, and display the identified portions of the percutaneous tool on the image data.

Provided in accordance with embodiments of the present disclosure is a method for identifying a percutaneous tool in image data. In an aspect of the present disclosure, an illustrative method includes receiving image data of at least a portion of a patient's body, identifying a potential distal portion of a percutaneous tool in the image data, identifying a potential shaft portion of the percutaneous tool within a predetermined distance from the identified potential distal portion of the percutaneous tool, determining a line from the identified potential distal portion of the percutaneous tool through the identified potential shaft portion of the percutaneous tool, identifying a potential remaining portion of the percutaneous tool in the image data based on the line, and displaying the identified potential distal, shaft, and remaining portions of the percutaneous tool on the image data.

In another aspect, the method further includes receiving characteristic data of the percutaneous tool, and identifying the remaining portion of the percutaneous tool in the image data is further based on the characteristic data of the percutaneous tool.

In a further aspect, the characteristic data of the percutaneous tool includes one or more of a length of the percutaneous tool, a diameter of the percutaneous tool, and a flexibility metric of the percutaneous tool.

In another aspect, the method further includes determining whether the identified potential distal, shaft, and remaining portions of the percutaneous tool correspond to a valid percutaneous tool.

In yet another aspect, the method further includes identifying a target location in the image data, determining a path from the entry point to the target location, determining a trajectory of the percutaneous tool based on an entry point and angle of insertion of the percutaneous tool into the patient's body, determining whether the trajectory of the percutaneous tool corresponds to the path, and displaying the trajectory and the path on the image data.

In a further aspect, if it is determined that the trajectory of the percutaneous tool does not correspond to the path, the method further includes determining a difference between the trajectory and the path, and displaying guidance for adjusting an angle of the percutaneous tool based on the determined difference between the trajectory and the path.

In another aspect, the percutaneous tool is an ablation needle, and the method further includes receiving configuration settings for an ablation procedure, identifying a position of a radiating portion of the percutaneous tool in the image data, determining a projected ablation zone based on the configuration settings and the identified position of the radiating portion of the percutaneous tool, and displaying the projected ablation zone on the image data.

In a further aspect, the method further includes receiving an indication that the radiating portion of the percutaneous tool has been activated, determining a progress of an ablation procedure based on the configuration settings and a time during which the percutaneous tool has been activated, and displaying an estimated ablated zone based on the determined progress of the ablation procedure.

In another aspect, the method further includes identifying an entry point of the percutaneous tool into the patient's body in the image data, determining a line in the image data between the entry point and the identified potential distal portion of the percutaneous tool, and displaying the determined line on the image data.

In yet another aspect, identifying the potential remaining portion of the percutaneous tool includes analyzing the image data to identify high intensity areas along the determined line, and including portions of the high intensity areas along a length of the determined line and within a radius of the determined line, and the radius is determined based on a diameter characteristic of the percutaneous tool.

In a further aspect, identifying the potential remaining portion of the percutaneous tool further includes excluding portions of the high intensity areas along the length of the determined line and outside of the radius of the determined line.

In another aspect, the distal portion of the percutaneous tool is identified based on characteristic data of the percutaneous tool.

In yet another aspect, the distal portion of the percutaneous tool is identified based on an electromagnetic sensor included in the percutaneous tool.

Provided in accordance with embodiments of the present disclosure is a system for identifying a percutaneous tool in image data. In an aspect of the present disclosure, an illustrative system includes a percutaneous tool, a display device, and a computing device including a processor, and a memory storing instructions which, when executed by the processor, cause the computing device to receive image data of at least a portion of a patient's body, identify a potential distal portion of a percutaneous tool in the image data, identify a potential shaft portion of the percutaneous tool within a predetermined distance from the identified potential distal portion of the percutaneous tool, determine a line from the identified potential distal portion of the percutaneous tool through the identified potential shaft portion of the percutaneous tool, identify a potential remaining portion of the percutaneous tool in the image data based on the line, and display the identified potential distal, shaft, and remaining portions of the percutaneous tool on the image data.

Provided in accordance with embodiments of the present disclosure is a non-transitory computer-readable storage medium storing a program for identifying a percutaneous tool in image data. In an aspect of the present disclosure, the program includes instructions which, when executed by a processor, cause a computing device to receive image data of at least a portion of a patient's body, identify a potential distal portion of a percutaneous tool in the image data, identify a potential shaft portion of the percutaneous tool within a predetermined distance from the identified potential distal portion of the percutaneous tool, determine a line from the identified potential distal portion of the percutaneous tool through the identified potential shaft portion of the percutaneous tool, identify a potential remaining portion of the percutaneous tool in the image data based on the line, and display the identified potential distal, shaft, and remaining portions of the percutaneous tool on the image data.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1:
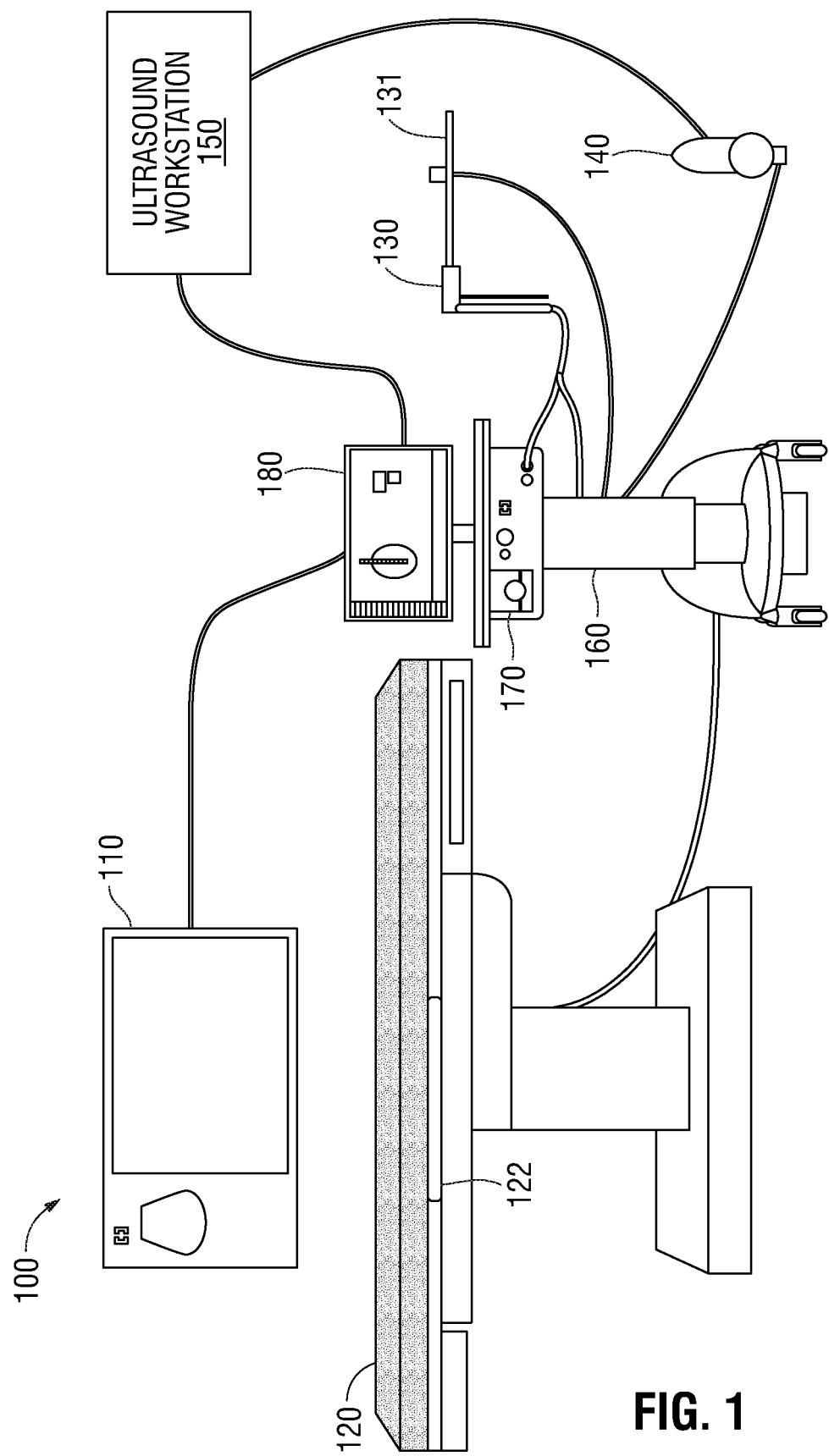
FIG. 1 is a schematic diagram of an exemplary system for planning and conducting a microwave ablation procedure, according to an embodiment of the present disclosure.

The present disclosure generally relates to systems and methods for identifying and segmenting medical instruments, such as ablation needles, in radiographic images. In particular, by determining a line based on a trajectory of a medical instrument inserted through a patient's skin and/or a line extending from a distal portion of an instrument, high intensity areas identified in radiographic images within a predetermined distance from the line may be segmented as part of the medical instrument, and high intensity areas more than the predetermined distance from the line may be excluded.

Radiographic images, such as computed tomography (CT) images, magnetic resonance imaging (MRI) images, cone beam computed tomography (CBCT) images, two-dimensional (2D) and/or three-dimensional (3D) X-ray images, 2D and/or 3D ultrasound images, and/or various other imaging modalities may be obtained during a medical procedure to identify placement of medical instruments, such as ablation needles, in a patient's body, and particularly, about a treatment site. While placement of medical instruments may be confirmed via visual inspection during open and/or laparoscopic surgical procedures, such visual inspection is often not possible during percutaneous procedures. As such, radiographic imaging techniques are used to guide and confirm placement of medical instruments. However, identification of the medical instruments in the radiographic images is not a perfect process, and, due to limited resolution and clarity of radiographic images, structures and/or objects other than the medical instruments may be misidentified as part of the medical instruments. Further, medical instruments inserted at an angle that crosses multiple imaging planes and/or image slices or traverse an area of significant interference, may be hard to identify in the radiographic images.

Identification of medical instruments in radiographic images may be significantly improved when characteristics, such as length, diameter, point of insertion, and/or trajectory of the medical instrument are taken into account when attempting to identify the medical instruments in the radiographic images. For example, by determining a line based on a trajectory of a medical instrument inserted through a patient's skin, it may be determined which high intensity areas identified in image data about the medical instrument's location should be included as part of the medical instrument, and which high intensity areas should be excluded. Then, when the position of the medical instrument, guidance may be provided for navigating the medical instrument to a target location. Once the medical instrument is placed at the target location, a projected ablation zone may be determined based on the location of a radiating portion of the ablation needle, and the projected ablation zone may be displayed to the clinician so that the clinician may visualize the ablation zone relative to the radiographic images to determine whether the ablation zone encompasses the entirety of the area the clinician is seeking to treat.

Methods for automated identification and segmentation of a percutaneous tool in radiographic images, such as CT images, providing guidance for navigating the percutaneous tool to a target location, as well as monitoring a progress of a treatment procedure, such as an ablation procedure, may be implemented as part of an electromagnetic navigation (EMN) system. Generally, in an embodiment, the EMN system may be used in planning and performing treatment of an area of the patient's body, such as the patient's lungs, by determining a path to a target location, such as a treatment location, inserting an ablation needle into the patient's body, and positioning the ablation needle proximate the target location. The EMN system may be configured to display various views of the patient's body, including the radiographic images and/or a three-dimensional (3D) model of the patient's body generated based the radiographic images.

With reference to FIG. 1, there is shown a system 100 usable for automated identification and segmentation of an ablation needle in radiographic images. System 100 may include a display device 110, a table 120 including an electromagnetic (EM) field generator 121, a treatment tool 130 including a distal radiating portion 131, an ultrasound sensor 140 connected to an ultrasound workstation 150, a peristaltic pump 160, and a computing device 180 attached to or in operable communication with a microwave generator 170. Display device 110 is configured to output instructions, images, and messages relating to the performance of the medical procedure.

Table 120 may be, for example, an operating table or other table suitable for use during a medical procedure, which includes EM field generator 121. EM field generator 121 is used to generate an EM field during the medical procedure and forms part of an EM tracking system that is used to track positions of medical instruments within the patient's body, such as by tracking a position of one or more EM sensors included in and/or coupled to treatment tool 130. EM field generator 121 may include various components, such as a specially designed pad to be placed under, or integrated into, table 120 or a patient bed. An example of such an EM tracking system is the AURORA™ system sold by Northern Digital Inc.

Treatment tool 130 is a medical instrument for percutaneously accessing and diagnosing and/or treating tissue at a target location. For example, treatment tool 130 may be an ablation needle having a microwave ablation needle or antenna that is used to ablate tissue. In other embodiments, treatment tool 130 may be a biopsy tool for obtaining a tissue sample at the target location. Those skilled in the art will recognize that various other types of percutaneous tools, including, for example, cannulas for guiding catheters or other tools to a treatment site may also be used without departing from the scope of the present disclosure. In embodiments where treatment tool 130 is an ablation needle, treatment tool 130 includes distal radiating portion 131, and may further include or be coupled to one or more EM sensors enabling the EM tracking system to track the location, position, and orientation (also known as the "pose") of treatment tool 130 inside the body of the patient. As explained in further detail below, treatment tool 130 may be described as having various portions. For example, when treatment tool 130 is inserted into a patient's body, treatment tool 130 may be described as having a portion inserted into the patient's body, and a portion external to the patient's body. The portion of treatment tool 130 inserted into the patient's body may further be divided into a portion inserted through the patient's skin—that is, the portion of treatment tool 130 that is in contact with the various layers of the patient's skin—and a remaining portion inserted into the patient's body—that is, the rest of treatment tool 130 inserted into the patient's body excluding the portion that is in contact with the various layers of the patient's skin. Likewise, the remaining portion of treatment tool 130 inserted into the patient's body may further be divided into a distal portion (which may include distal radiating portion 131), and a proximal portion. The distal portion may be the portion of treatment tool 130 inserted the furthest into the patient's body.

Peristaltic pump 160 may be configured to pump fluid through treatment tool 130 to cool treatment tool 130 during the medical procedure. Microwave generator 170 may be configured to output microwave energy to treatment tool 130 via distal radiating portion 131. Computing device 180 may be, for example, a laptop computer, desktop computer, tablet computer, or other similar device. Computing device 180 may be configured to control microwave generator 170, peristaltic pump 160, a power supply (not shown), and/or any other accessories and peripheral devices relating to, or forming part of, system 100. In some embodiments, microwave generator 170 controls the operation of peristaltic pump 160. While the present disclosure describes the use of system 100 in a surgical environment, it is also envisioned that some or all of the components of system 100 may be used in alternative settings, for example, an imaging laboratory and/or an office setting.

In addition to the EM tracking system, the surgical instruments used during the medical procedure, such as treatment tool 130, may also be visualized by using CT and/or ultrasound imaging. Ultrasound sensor 140, such as an ultrasound wand, may be used to image the patient's body during the medical procedure to visualize the location of the surgical instruments, such as treatment tool 130, inside the patient's body. Ultrasound sensor 140 may have an EM tracking sensor embedded within or attached to the ultrasound wand, for example, a clip-on sensor or a sticker sensor. Ultrasound sensor 140 may be positioned in relation to treatment tool 130 such that treatment tool 130 is at an angle to the ultrasound image plane, thereby enabling the clinician to visualize the spatial relationship of treatment tool 130 with the ultrasound image plane and with objects being imaged. Further, the EM tracking system may also track the location of ultrasound sensor 140. In some embodiments, one or more ultrasound sensors 140 may be placed inside the patient's body. EM tracking system may then track the location of such ultrasound sensors 140 and treatment tool 130 inside the patient's body. Ultrasound workstation 150 may be used to configure, operate, and/or view images captured by ultrasound sensor 140. Likewise, computing device 180 may be used to configure, operate, and/or view images captured by ultrasound sensor 140, either directly or relayed via ultrasound workstation 150.

Various other surgical instruments or surgical tools, such as LIGASURE® devices, surgical staplers, etc., may also be used during the performance of a medical procedure. In embodiments where treatment tool 130 is a microwave ablation needle, the microwave ablation needle is used to ablate a lesion or tumor (hereinafter referred to as a "target location") by using microwave energy to heat tissue in order to denature or kill cancerous cells. The construction and use of a system including such an ablation needle is more fully described in co-pending U.S. Patent Application Publication No. 2016/0058507, entitled MICROWAVE ABLATION SYSTEM, filed on Aug. 26, 2014, by Dickhans, U.S. Pat. No. 9,247,992, entitled MICROWAVE ABLATION CATHETER AND METHOD OF UTILIZING THE SAME, filed on Mar. 15, 2013, by Latkow et al., and U.S. Pat. No. 9,119,650, entitled MICROWAVE ENERGY-DELIVERY DEVICE AND SYSTEM, filed on Mar. 15, 2013, by Brannan et al., the entire contents of each of which are hereby incorporated by reference.

As noted above, the location of treatment tool 130 within the body of the patient may be tracked during the medical procedure. An example method of tracking the location of treatment tool 130 is by using the EM tracking system, which tracks the location of treatment tool 130 by tracking sensors, such as EM sensors, coupled to or incorporated in treatment tool 130. Various types of sensors may be used, such as a printed sensor, the construction and use of which is more fully described in co-pending U.S. Patent Application Publication No. 2016/017487314/919,950, entitled "MEDICAL INSTRUMENT WITH SENSOR FOR USE IN A SYSTEM AND METHOD FOR ELECTROMAGNETIC NAVIGATION", filed Oct. 22, 2015, by Greenburg et al., the entire contents of which are incorporated herein by reference. A percutaneous treatment system similar to the above-described system 100 is further described in co-pending U.S. Patent Application Publication No. 2016/0317224, entitled "MICROWAVE ABLATION PLANNING AND PROCEDURE SYSTEMS", filed on Apr. 15, 2016, by Girotto et al., the entire contents of which are incorporated herein by reference.

While the above-described system 100 uses a microwave generator 170 to provide microwave energy to treatment tool 130, those skilled in the art will appreciate that various other types of generators and tools may be used without departing from the scope of the present disclosure. For example, radio frequency (RF) ablation tools receiving RF energy from RF generators may be substituted for the microwave generators and ablation tools described above.

Figure 2:
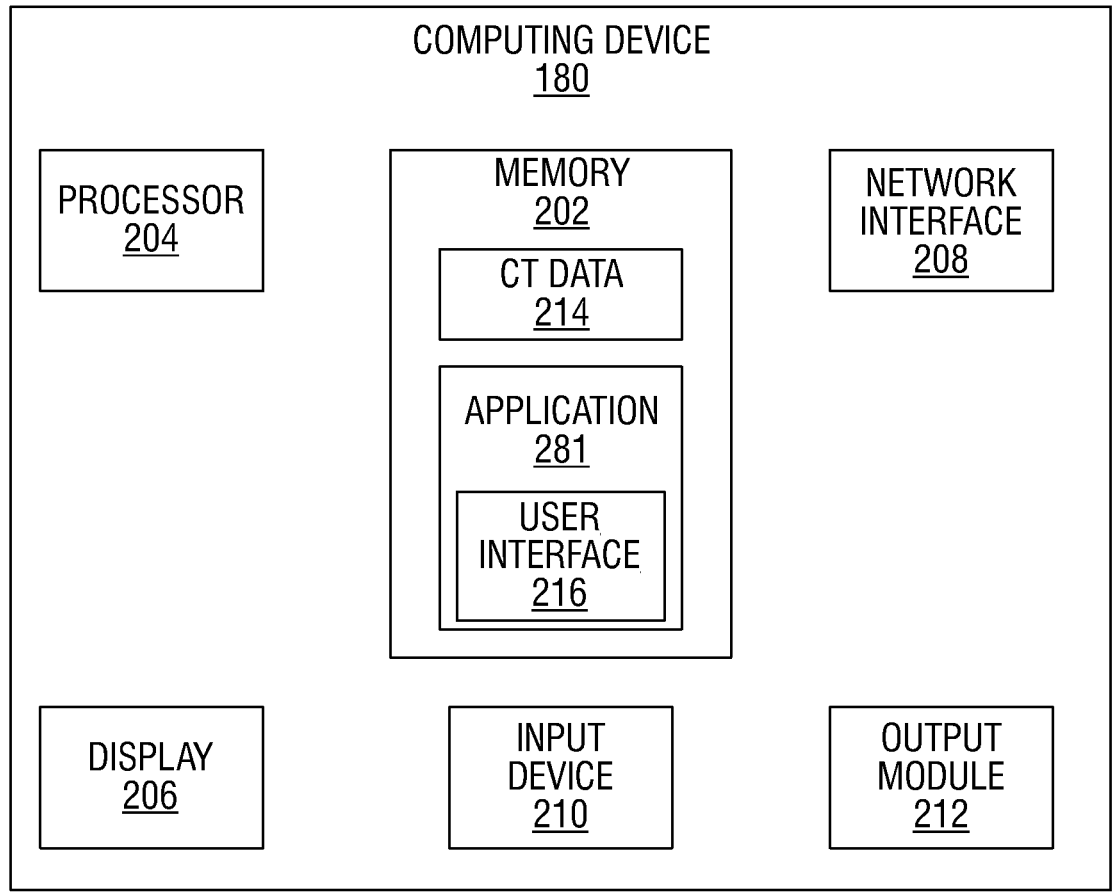
FIG. 2 is a simplified block diagram of a computing device forming part of the system of FIG. 1, according to an embodiment of the present disclosure.

With reference to FIG. 2, there is shown a simplified block diagram of computing device 180. Computing device 180 may include at least one memory 202, one or more processors 204, a display 206, a network interface 208, one or more input devices 210, and/or an output module 212. Memory 202 may store an application 281 and/or image data 214. Application 281 may, when executed by processor 204, cause display 206 to display a user interface 216. Application 281 may also provide an indication of the location of treatment tool 130 in relation to the target location, as well as the size, shape, and location of an ablation zone, as described further below.

Memory 202 may include any non-transitory computer-readable storage medium for storing data and/or software that is executable by processor 204 and which controls the operation of computing device 180. In an embodiment, memory 202 may include one or more solid-state storage devices such as flash memory chips. Alternatively, or in addition to the one or more solid-state storage devices, memory 202 may include one or more mass storage devices connected to processor 204 through a mass storage controller (not shown) and a communications bus (not shown). Although the description of computer-readable media included herein refers to a solid-state storage device, it should be appreciated by those skilled in the art that computer-readable storage media may be any available media that can be accessed by processor 204. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 180.

Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with computing device 180, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Figure 3A:
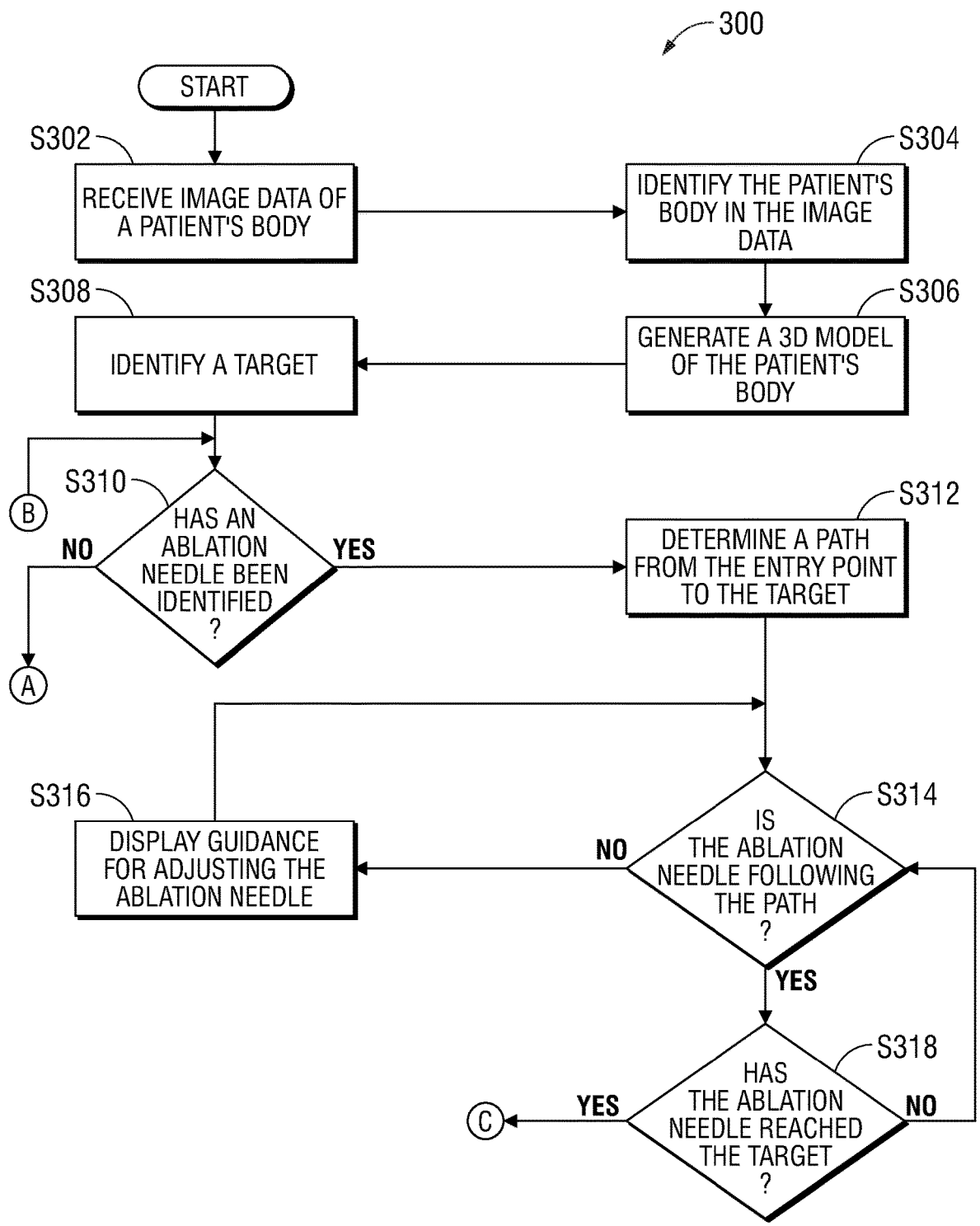
FIGS. 3A-3C show a flowchart of an exemplary method for planning and conducting a microwave ablation procedure, according to an embodiment of the present disclosure.
Figure 3B:
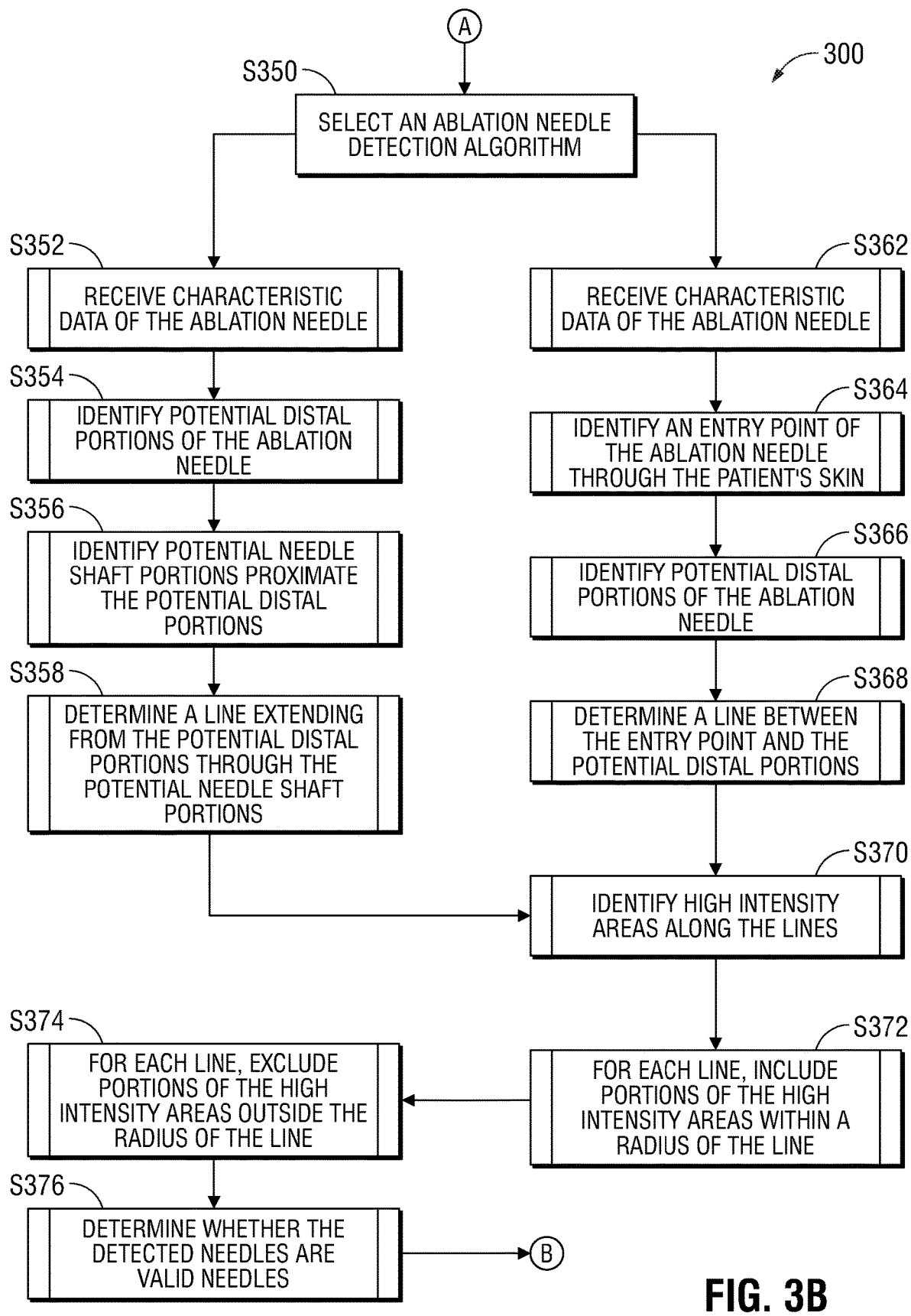
Figure 3C:
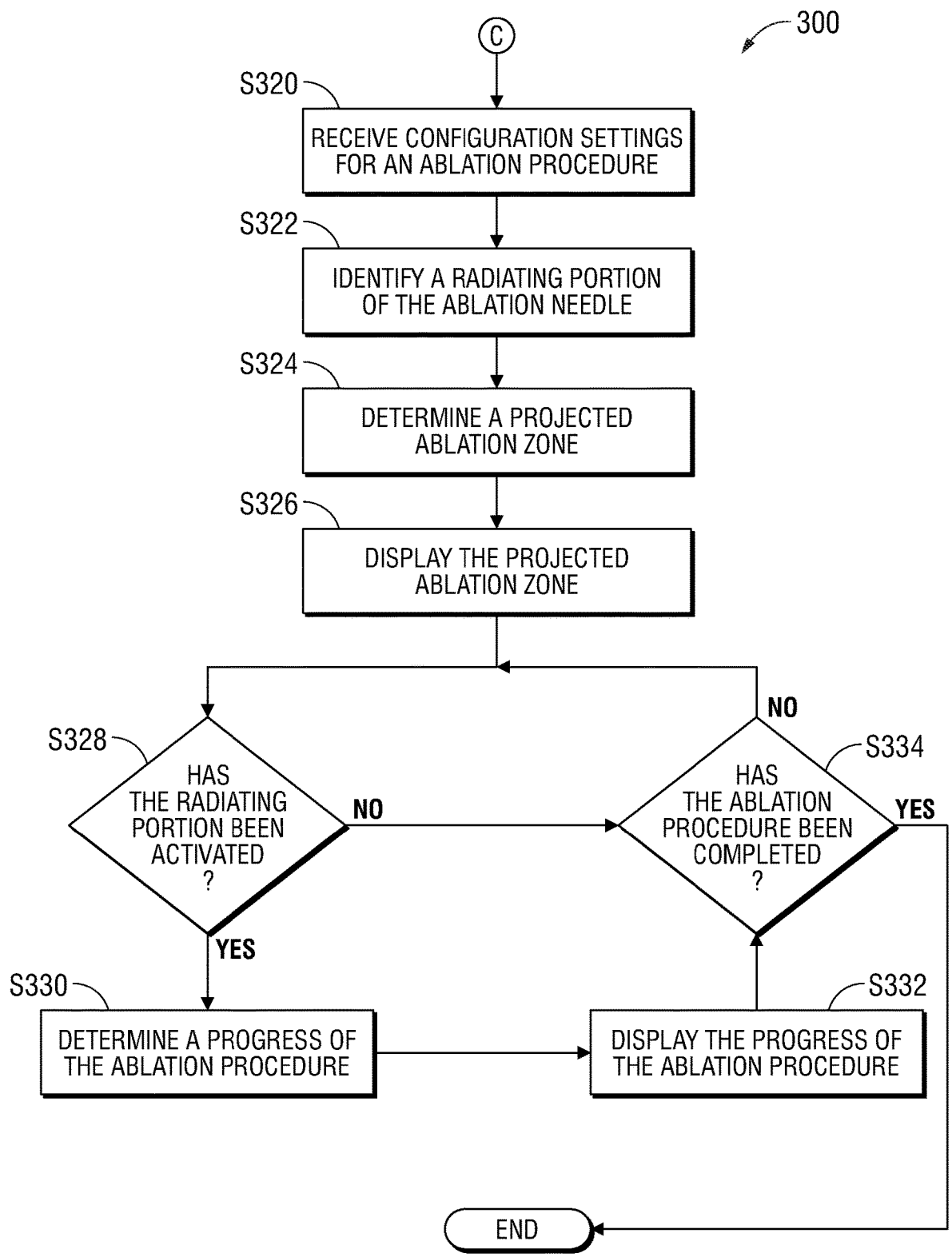

Turning now to FIGS. 3A-3C, there is shown a flowchart of an exemplary method 300 of automated identification and segmentation of an ablation needle in radiographic images, and providing guidance for navigating the ablation needle to a target location, according to an embodiment of the present disclosure. Method 300 may be performed, for example, by using system 100, described above. In particular, application 281, executing on computing device 180, may be used to perform, or cause other components of system 100 to perform, the steps of method 300. While the various steps of method 300 are described below in an exemplary sequence, those skilled in the art will recognize that some or all of the steps may be performed in a different order, repeated, and/or omitted without departing from the scope of the present disclosure.

Starting at step S302 of FIG. 3A, application 281 receives image data of a patient's body. The image data may be radiographic image data, such as CT image data, MRI image data, CBCT image data, X-ray image data, ultrasound image data, etc. For exemplary purposes, CT image data will be used in the description provided below. The image data may be received directly from an imaging device, such as a CT scanner, and/or may have previously been stored in memory 202 of computing device 180. The image data may be received at the start of the medical procedure, and/or during the performance of the medical procedure. For example, multiple sets of image data may be received at various times during the medical procedure when identification of an ablation needle is requested, as described further below.

Additionally, the image data may be used for pre-procedural purposes, such as for identifying the patient's body in the image data at step S304, and generating a 3D model of the patient's body at step S306. The 3D model of the patient's body may include one or more portions of the patient's body, and particularly, may include the portion of the patient's body where the medical procedure will be performed, e.g. where the target location is. In the example described hereinbelow, the image data include a portion of the patient's chest, and thus the 3D model generated at step S306 is of a portion of the patient's chest.

After generating the 3D model, or concurrently therewith, application 281, at step S308, processes the image data to identify a target location. In embodiments, the clinician provides input, such as via input device 210 of computing device 180 to identify the target location. For example, the clinician may review the image data received at step S302 and/or the 3D model generated at step S306 and select or mark one or more target locations. Application 281 may further determine one or more recommended entry points where treatment tool 130 should be inserted through the patient's skin to enable access to the target location identified at step S308. Application 281 may then cause display device 110 and/or display 206 to display guidance for inserting treatment tool 130 through the patient's skin.

Thereafter, at step S310, application 281 determines whether treatment tool 130 has been identified in the image data. If it is determined that treatment tool 130 has not been identified ("No" at step S310), processing proceeds to step S350 (described below with reference to FIG. 3B.) Alternatively, if it is determined that treatment tool 130 has been identified ("Yes" at step S310), processing proceeds to step S312.

Turning now to FIG. 3B, at step S350 application 281 selects an ablation needle detection algorithm to use. Various algorithms may be used to detect an ablation needle in image data. For purposes of the present disclosure, two ablation needle detection algorithms will be described. For example, steps S352-S358 and S370-S376 may correspond to a first exemplary algorithm, while steps S362-S368 and S370-S376 may correspond to a second exemplary algorithm. However, those skilled in the art will recognize that various other ablation needle detection algorithms may also be used without departing from the scope of the present disclosure.

Processing of a first exemplary algorithm may start at step S352 where application 281 receives characteristic data of treatment tool 130. The characteristic data may include a type of treatment tool 130, such as an ablation needle, being used, a length of treatment tool 130, a diameter of treatment tool 130, a flexibility metric (such as Young's modulus) of treatment tool 160, a location of one or more EM sensors included in treatment tool 130, a location of distal radiating portion 131 in treatment tool 130, locations of radiolucent fiducial markers and/or features designed to be visible under ultrasound imaging, etc. The characteristic data may be accessed by application 281 from memory 202, may be inputted by the clinician via input device 210, and/or may be provided to application 281 by treatment tool 130 and/or generator 170.

Thereafter, at step S354, application 281 identifies one or more potential distal portions of treatment tool 130. For example, application 281 may process the image data received at step S302 and/or additional image data received subsequently and throughout the medical procedure, to identify one or more distal portions of treatment tool 130, such as based on the characteristic data of treatment tool 130 received at step S352. In embodiments, application 281 may process only a portion of the image data that includes the patient's body, an area proximate the target location determined at step S308, and/or an area proximate the recommended entry points determined at step S308. For example, application 281 may identify one or more areas of high intensity pixels having a shape similar to an eclipse as potential distal portions of treatment tool 130. In embodiments, application 281 may determine a depth that treatment tool 130 is inserted into the patient's body, and may then seek to identify potential distal portions of treatment tool 130 that are about a corresponding distance from the recommended entry points determined at step S308. The depth that treatment tool 130 is inserted into the patient's body may be determined based on lines and/or markers on treatment tool 130 (not shown in FIG. 1), and/or one or more EM sensors included in treatment tool 130. Additionally or alternatively, application 281 may identify the distal portion of treatment tool 130 based on the location of the one or more EM sensors, radiolucent fiducial markers, and/or other radiopaque elements included in treatment tool 130. For example, the position of the one or more EM sensors and/or radiolucent fiducial markers included in treatment tool 130 relative to the distal portion of treatment tool 130 may be known, and thus the location of the distal portion of treatment tool 130 may be determined based on a detected position of the one or more EM sensors and/or radiolucent fiducial markers.

Next, at step S356, application 281 identifies one or more potential shaft portions of treatment tool 130 proximate the potential distal portions of treatment tool 130 identified at step S354. For example, application 281 may further process the image data to identify areas of high intensity pixels within a predetermined distance of the identified potential distal portions of treatment tool 130. In embodiments, application 281 may identify areas of high intensity pixels within 48 millimeters (mm) of the identified potential distal portions of treatment tool 130. In further embodiments, application 281 may identify areas of high intensity pixels more than 44 mm but less than 48 mm from the identified potential distal portions of treatment tool 130.

Figure 5A:
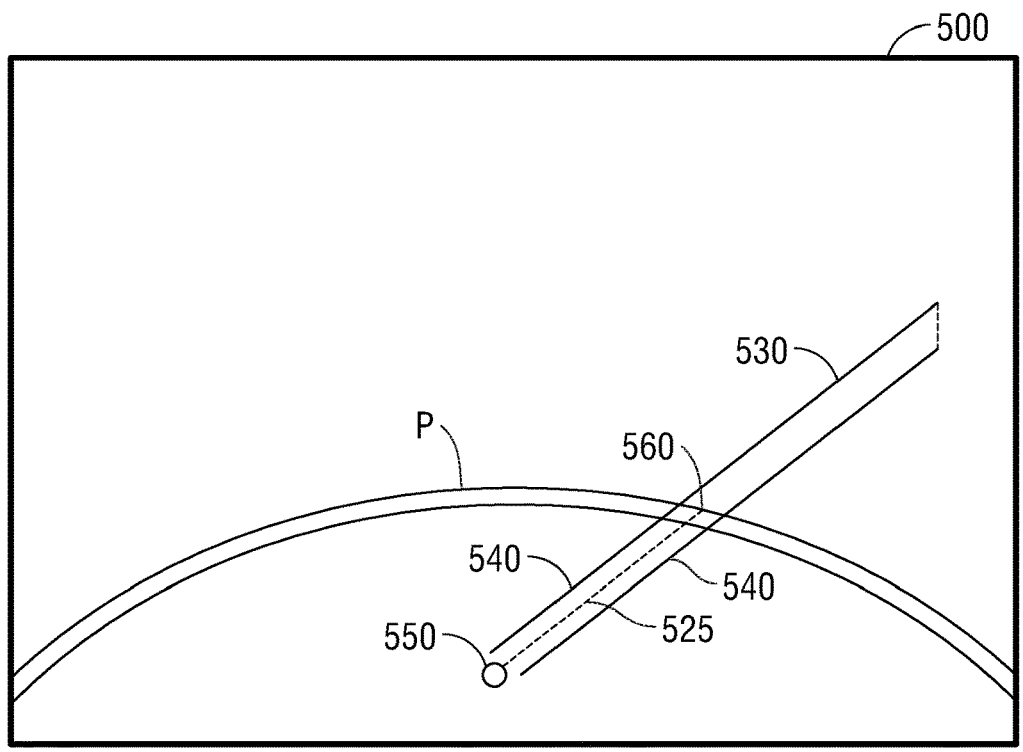
FIG. 5A shows an exemplary graphical user interface which may be displayed by the computing device of FIG. 2 while a medical instrument is being identified, according to an embodiment of the present disclosure.

Thereafter, at step S358, application 281 determines a line extending from the potential distal portions of treatment tool 130 identified at step S354 through the potential shaft portions of treatment tool 130 identified at step S356. In embodiments, application 281 may determine a line extending from each of the identified potential distal portions of treatment tool 130 through each of its corresponding identified potential shaft portions of treatment tool 130. In further embodiments, application 281 may only determine a line extending from each of the identified potential distal portions of treatment tool 130 through corresponding identified potential shaft portions of treatment tool 130 that are in line with at least one of the recommended entry points identified at step S308. For example, as shown in FIG. 5A, application 281 may determine a line 525 in the image data extending from an identified potential distal portion 550 through potential identified shaft portions to a recommended entry point 560. Alternatively or additionally, application 281 may determine a plurality of lines 540 in the image data corresponding to outlines of tool 530 (representing treatment tool 130), based on the image data and/or the characteristic data.

Next, at step S370, application 281 identifies high intensity areas in the image data along each determined line 525. For example, application 281 may identify bright spots and/or areas in the image data along a length of each determined line 525. High intensity areas may be indicative of metallic objects, such as treatment tool 130. Application 281 then, at step S372, includes portions of the high intensity areas within a radius of each determined line 525 as part of an identified potential treatment tool 130 in the image data. The portions of the high intensity areas within the radius of each determined line 525 may correspond to potential remaining portions of treatment tool 130. For example, application 281 may include all high intensity areas within a radius determined based on the characteristic data (received at step S352) as part of the identified potential treatment tool 130. In an embodiment where application 281 determines a plurality of lines 540 at step S370, application 281 may include only high intensity areas within the area included in the outlines of treatment tool 130, as indicated by the determined lines 540, as part of the identified potential treatment tool 130.

Likewise, application 281, at step S374, excludes portions of the high intensity areas outside of the radius of each determined line 525 from the identified potential treatment tool 130 in the image data. In an embodiment where application 281 determines a plurality of lines 540 at step S370, application 281 may exclude all high intensity areas not within the area included in the outlines of treatment tool 130, as indicated by the determined lines 540, from being part of the identified potential treatment tool 130. Application 281 may further fill in any gaps or omissions in the area within the radius from each determined line 525, and thus may be expected to be included in the identified potential treatment tool 130.

Next, at step S376, application 281 determines whether each identified potential treatment tool 130 is a valid or invalid treatment tool 130. For example, as noted above, a line is determined from each of the identified potential distal portions of treatment tool 130 through corresponding identified potential shaft portions of treatment tool 130. Thus, a plurality of potential treatment tools 130 may be identified. Application 281 may further process the image data based on the characteristic data received at step S352 to determine automatically and/or via input from the clinician, which, if any, of the potential treatment tools 130 identified in the image data is a valid treatment tool 130. In embodiments, multiple treatment tools 130 may be inserted into the patient's body and identified concurrently, thus in some embodiments, application 281 may determine at step S376 that multiple potential treatment tools 130 are valid treatment tools 130. After all potential treatment tools 130 are analyzed and determined to be valid or invalid, processing returns to step S310, where it is again determined whether treatment tool 130 has been identified in the image data.

Processing of a second exemplary algorithm may start at step S362 where application 281 receives characteristic data of treatment tool 130. As with the first exemplary algorithm, the characteristic data may include a type of treatment tool 130, such as an ablation needle, being used, a length of treatment tool 130, a diameter of treatment tool 130, a flexibility metric (such as Young's modulus) of treatment tool 160, a location of one or more EM sensors included in treatment tool 130, a location of distal radiating portion 131 in treatment tool 130, locations of radiolucent fiducial markers and/or features designed to be visible under ultrasound imaging, etc. The characteristic data may be accessed by application 281 from memory 202, may be inputted by the clinician via input device 210, and/or may be provided to application 281 by treatment tool 130 and/or generator 170.

Figure 5B:
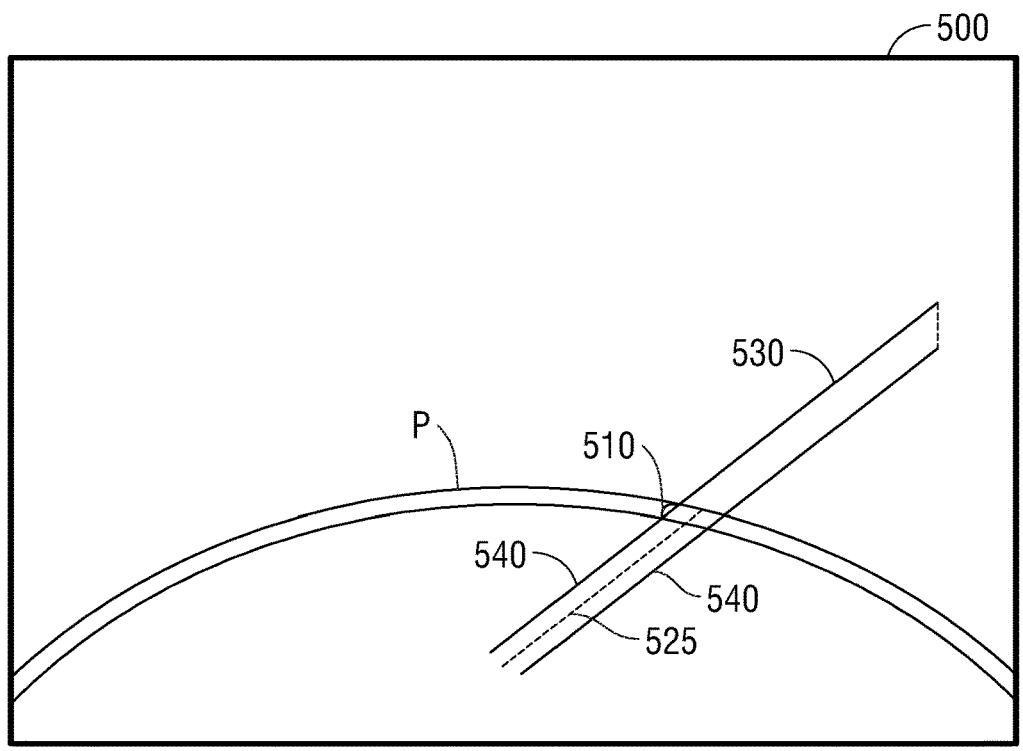
FIG. 5B shows another exemplary graphical user interface which may be displayed by the computing device of FIG. 2 while a medical instrument is being identified, according to an embodiment of the present disclosure.

Thereafter, application 281 may receive additional image data of the patient's body and, at step S364, process the additional image data to identify a portion of treatment tool 130 inserted through the patient's skin. For example, application 281 may analyze image data of an area proximate the recommended entry points determined at step S308 to identify a portion of treatment tool 130 inserted through the patient's skin. Application 281 may further determine an angle of insertion of treatment tool 130 through the patient's skin based on the identified portion of treatment tool 130, and may thus determine a trajectory of treatment tool 130 based on the entry point of treatment tool 130 through the patient's skin and the angle of insertion. For example, as shown in FIG. 5B, application 281 may analyze image data of a patient's body ("P") to identify a portion 510 of a tool 530 inserted through the skin of body P.

Next, at step S366, application 281 identifies potential distal portions of treatment tool 130 in the image data. Similar to step S354, application 281 may process the image data received at step S302 and/or additional image data received subsequently and throughout the medical procedure, to identify one or more distal portions of treatment tool 130, such as based on the characteristic data of treatment tool 130 received at step S362. In embodiments, application 281 may process only a portion of the image data that includes the patient's body, an area proximate the target location determined at step S308, and/or an area proximate the entry point determined at step S364. For example, application 281 may identify one or more areas of high intensity pixels having a shape similar to an eclipse as potential distal portions of treatment tool 130. In embodiments, application 281 may determine a depth that treatment tool 130 is inserted into the patient's body, and may then seek to identify potential distal portions of treatment tool 130 that are about a corresponding distance from the entry point determined at step S364. The depth that treatment tool 130 is inserted into the patient's body may be determined based on lines and/or markers on treatment tool 130 (not shown in FIG. 1), and/or one or more EM sensors included in treatment tool 130. Additionally or alternatively, application 281 may identify the distal portion of treatment tool 130 based on the location of the one or more EM sensors, radiolucent fiducial markers, and/or other radiopaque elements included in treatment tool 130. For example, the position of the one or more EM sensors and/or radiolucent fiducial markers included in treatment tool 130 relative to the distal portion of treatment tool 130 may be known, and thus the location of the distal portion of treatment tool 130 may be determined based on a detected position of the one or more EM sensors and/or radiolucent fiducial markers.

Thereafter, at step S368, application 281 determines a line between the entry point determined at step S364 and each of the potential distal portions of treatment tool 130 identified at step S366. For example, as shown in FIG. 5B, application 281 may determine a line 525 in the image data extending along a central axis of tool 530 (representing treatment tool 130) from a portion 510 of treatment tool 130 identified in the patient's skin to an identified potential distal portion of treatment tool 130, based on the characteristic data of treatment tool 130 received at step S362. An angle and/or trajectory of line 525 may be based on the angle and/or trajectory of treatment tool 130 inserted through the patient's skin as determined at step S364. Alternatively or additionally, application 281 may determine a plurality of lines 540 in the image data corresponding to outlines of tool 530 (representing treatment tool 130), based on the image data and/or the characteristic data. Thereafter, processing proceeds to step S370, which is performed as described above in the description of the first exemplary algorithm.

Figure 6:
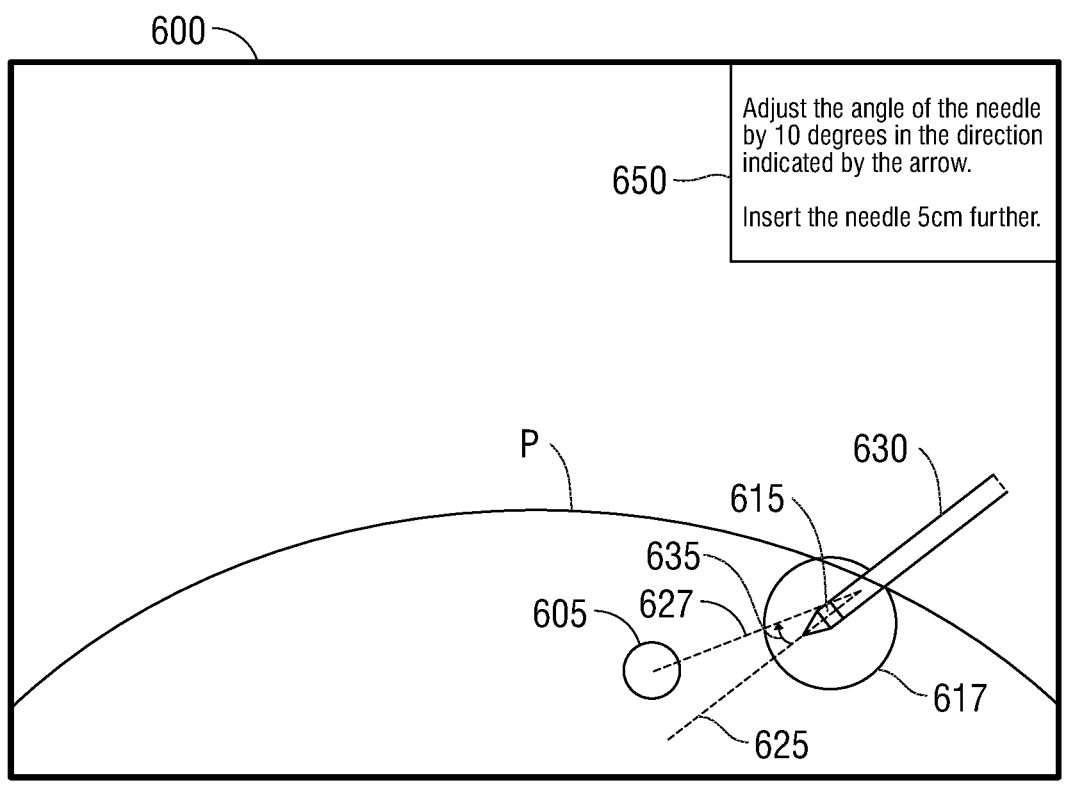
FIG. 6 shows an exemplary graphical user interface which may be displayed by the computing device of FIG. 2 while a medical instrument is being navigated, according to an embodiment of the present disclosure.

Returning now to FIG. 3A, at step S312, application 281 determines a path from the entry point where treatment tool 130 is inserted though the patient's skin (as identified at step S308 and/or step S364) to the target location identified at step S308. For example, as shown in FIG. 6, application 281 may determine a path 627 from the entry point to a target 605.

Thereafter, at step S314, application 281 determines whether treatment tool 130 is following the path determined at step S312. In embodiments, application 281 may receive further image data of one or more portions of the patient's body, and may determine an angle of insertion of treatment tool 130 through the patient's skin, and thus a trajectory of treatment tool 130. Application 281 may then compare the trajectory of treatment tool 130 with the path determined at step S312 to determine whether the trajectory of treatment tool 130 corresponds to the path determined at step S312, and thereby determine whether treatment tool 130 is following the path determined at step S312. For example, as shown in FIG. 6, application 281 may determine a trajectory 625 of tool 630 (representing treatment tool 130). Application 281 may further determine a difference between the trajectory 625 of tool 630 and the path 627. If it is determined that treatment tool 130 is not following the path ("No" at step S314), processing proceeds to step S316, where application 281 generates and causes display device 110 and/or display 206 to display guidance for adjusting the position and/or angle of treatment tool 130. For example, as shown in FIG. 6, application 281 may generate instructions to guide the clinician on how to adjust the position of treatment tool 130 and/or navigate treatment tool 130 to the target location (represented by target 605). In the example shown in FIG. 6, application 281 causes display device 110 and/or display 206 to display guidance 650 instructing the clinician to adjust the angle of treatment tool 130 by 10 degrees in the direction shown by an arrow 635, and to insert treatment tool 130 5 cm further into the patient's body. Thereafter, processing returns to step S314, where application 281 again determines if treatment tool 130 is following the path determined at step S312. If it is determined at step S314 that treatment tool 130 is following the path ("Yes" at step S314), processing proceeds to step S318.

At step S318, application 281 determines whether treatment tool 130 has reached the target location. For example, application 281 may receive further image data of the portion of the patient's body, and may again identify treatment tool 130 in the image data, as described above, to determine whether treatment tool 130 has been placed at the target location. Additionally or alternatively, application 281 may receive input from the clinician, such as via input device 210 of computing device 180, indicating that treatment tool 130 has been placed at the target location. If application 281 determines that treatment tool 130 has not reached the target location ("No" at step S318), processing returns to step S314. Alternatively, if application 281 determines that treatment tool 130 has reached the target location ("Yes" at step S318), processing proceeds to step S320.

Turning now to FIG. 3C, at step S320, application 281 may receive configuration settings for an ablation procedure. In some embodiments, the configuration settings are received earlier in the medical procedure or are preconfigured prior to the start of the medical procedure. The configuration settings may include a location of the ablation procedure, identified anatomical structures proximate the location of the ablation procedure, a duration of the ablation procedure, a wattage that will be output by treatment tool 130 during the ablation procedure, modeled ablation procedure performance, etc. The configuration settings may be preconfigured, such as included in or based on a treatment plan configured by a clinician prior to the start of the medical procedure, and/or may be input by the clinician at the start of, or during, the medical procedure, such as by using input device 210 of computing device 180.

Next, at step S322, application 281 identifies radiating portion 131 of treatment tool 130. For example, application 281 may determine a location of radiating portion 131 based on the characteristic data of treatment tool 130 received at step S321. Thereafter, at step S324, application 281 determines a projected ablation zone. The determination of the projected ablation zone may be based on the identified location of radiating portion 131 and the configuration settings for the ablation procedure received at step S320. Application 281 may then, at step S326, cause display 206 of computing device 180 and/or display device 110 to display the projected ablation zone. The projected ablation zone may be displayed on the image data. Alternatively or in addition, the projected ablation zone may be displayed on the 3D model generated at step S306. For example, as shown in FIG. 6, a projected ablation zone 617 may be displayed as centered on a radiating portion 615 (representing radiating portion 131) of tool 630. As will be appreciated by those skilled in the art, projected ablation zone 617 may be selectively displayed at any point during the medical procedure, and is not necessarily limited to being displayed only after treatment tool is placed at the target location. Thus, as shown in FIG. 6, projected ablation zone 617 is displayed while tool 630 is being navigated to target 605, such that the clinician may see the area of tissue that is within the projected ablation zone based on a current location of treatment tool 130 and the configuration settings for the ablation procedure.

Thereafter, at step S328, it is determined whether radiating portion 131 of treatment tool 130 has been activated. For example, treatment tool 130 and/or generator 170 may notify computing device 180, and thus application 281, that a button, trigger, and/or activation switch has been activated allowing microwave energy to be emitted from radiating portion 131 of treatment tool 130. If it is determined that radiating portion 131 has not been activated ("No" at step S328), processing proceeds to step S334.

Alternatively, if it is determined that radiating portion 131 has been activated ("Yes" at step S328), processing proceeds to step S330 where application 281 determines a progress of an ablation procedure. The determination of the progress of the ablation procedure may be based on the configuration settings received at step S320, the projected ablation zone determined at step S326, and/or an elapsed time since the radiating portion was activated. Thereafter, at step S332, application 281 may display an estimated progress of the ablation procedure. For example, application 281 may cause display 206 of computing device 180 and/or display device 110 to display the estimated progress of the ablation zone. Similar to the projected ablation zone 617 displayed at step S326, the estimated progress of the ablation procedure may be displayed on the image data and/or the 3D model.

Next, at step S334, application 281 determines whether the ablation procedure has been completed. The determination whether the ablation procedure has been completed may be based on the estimated progress of the ablation procedure determined at step S332 and/or the configuration settings received at step S320. If it is determined that the ablation procedure has not been completed ("No" at step S334), processing returns to step S328. Alternatively, if it is determined that the ablation procedure has been completed ("Yes" at step S334), processing ends.

Figure 4A:
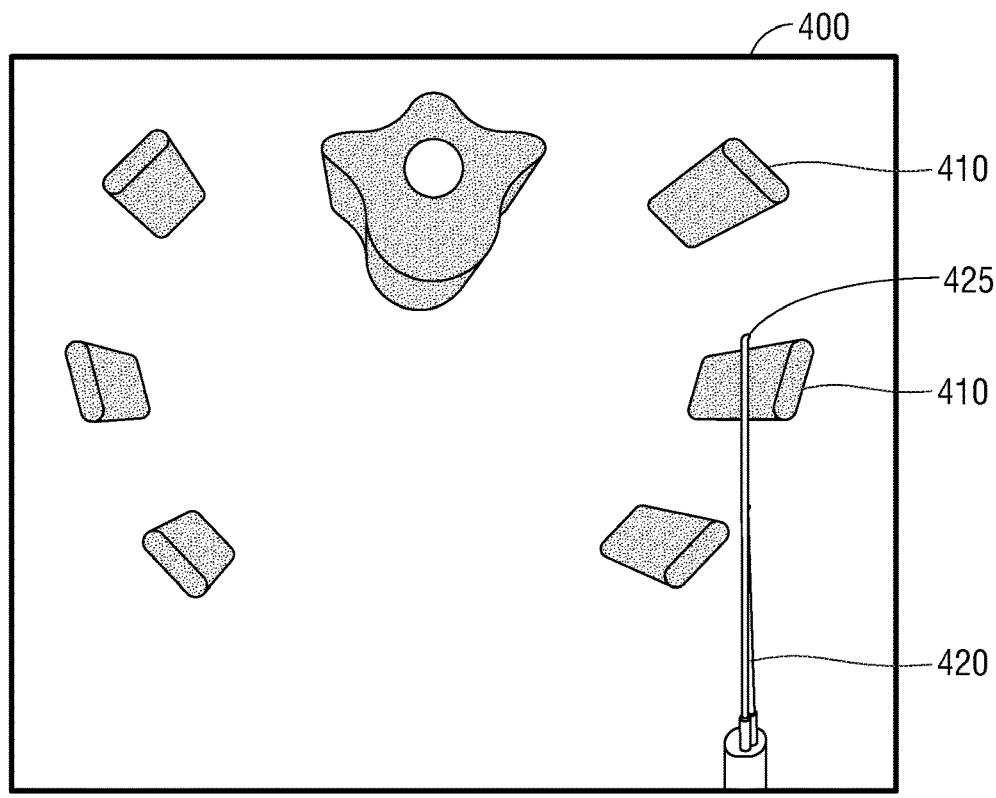
FIGS. 4A and 4B show exemplary graphical user interfaces that may be displayed by the computing device of FIG. 2 during an ablation procedure, according to an embodiment of the present disclosure.

Turning now to FIG. 4A, there is shown an exemplary graphical user interface (GUI) 400 that may be displayed by computing device 180 and/or display device 110 at various times during the above-described medical procedure. GUI 400 may include, or be based on, the image data received at step S302 and/or the 3D model generated at step S304 of method 300 of FIG. 3. GUI 400 may show physiological structures 410 and identified portions 420 of treatment tool 130. Physiological structures 410 may be any physiological structures identifiable in the image data and/or 3D model that are relevant to the medical procedure, and may be selectively displayed based on the clinician's preference.

Figure 4B:
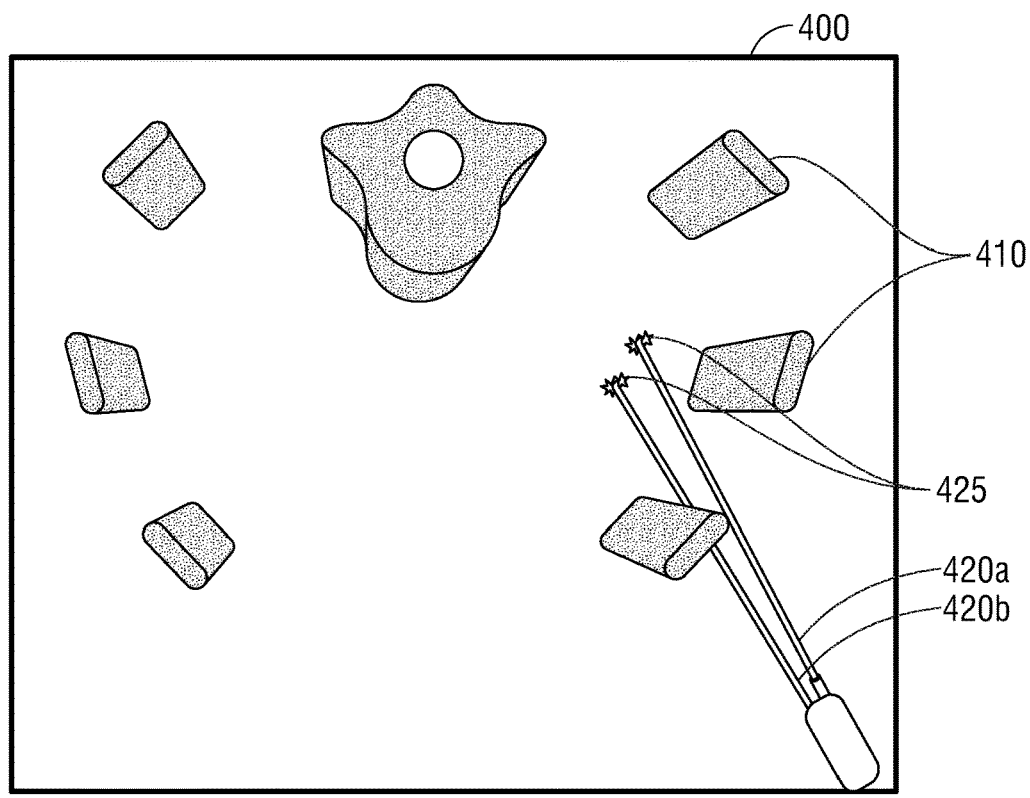

FIG. 4B shows another exemplary GUI 400 including the same physiological structures 410. GUI 400 of FIG. 4B shows an embodiment where a plurality of treatment tools is inserted into the patient concurrently, and thus includes a plurality of identified portions 420a, 420b of treatment tools 130. GUI 400 also shows an identified radiating portion 425 of identified portion 420a of treatment tool 130.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure.

What is claimed is:

1. A method for identifying a percutaneous tool in image data, the method comprising:
receiving image data of at least a portion of a patient's body;
identifying an entry point of a percutaneous tool inserted through the patient's skin in the image data;
analyzing a portion of the image data including the entry point of the percutaneous tool inserted through that patient's skin to identify a portion of the percutaneous tool in contact with one or more layers of the patient's skin;
determining a trajectory of the percutaneous tool based on the identified portion of the percutaneous tool in contact with the one or more layers of the patient's skin;
identifying, in the image data, a remaining portion of the percutaneous tool inserted within the patient's body excluding the portion of the percutaneous tool in contact with the one or more layers of the skin based on the identified entry point and the determined trajectory of the percutaneous tool; and displaying the identified portions of the percutaneous tool on the image data.

2. The method according to claim 1, further comprising receiving characteristic data of the percutaneous tool, wherein identifying the remaining portion of the percutaneous tool in the image data is further based on the characteristic data of the percutaneous tool.

3. The method according to claim 2, wherein the characteristic data of the percutaneous tool includes one or more of:
a length of the percutaneous tool; or
a flexibility metric of the percutaneous tool.

4. The method according to claim 1, wherein determining a trajectory of the percutaneous tool based on the identified portion of the percutaneous tool in contact with the one or more layers of the patient's skin includes:
determining an angle of insertion of the identified portion of the percutaneous tool in contact with the one or more layers of the patient's skin; and
determining a trajectory of the percutaneous tool based on the angle of insertion of the identified portion of the percutaneous tool in contact with the one or more layers of the patient's skin.

5. The method according to claim 1, further comprising:
identifying a target location in the image data;
determining a path from the entry point to the target location;
determining whether the trajectory of the percutaneous tool corresponds to the path; and
displaying the identified portions of the percutaneous tool, the trajectory, and the path on the image data.

6. The method according to claim 5, wherein if it is determined that the trajectory of the percutaneous tool does not correspond to the path, the method further comprises:
determining a difference between the trajectory and the path; and
displaying guidance for adjusting an angle of the percutaneous tool based on the determined difference between the trajectory and the path.

7. The method according to claim 1, further comprising:
receiving configuration settings for an ablation procedure;
identifying a position of a radiating portion of the percutaneous tool in the image data;
determining a projected ablation zone based on the configuration settings and the identified position of the radiating portion of the percutaneous tool; and
displaying the projected ablation zone on the image data.

8. The method according to claim 7, further comprising:
receiving an indication that the radiating portion of the percutaneous tool has been activated;
determining a progress of an ablation procedure based on the configuration settings and a time during which the percutaneous tool has been activated; and
displaying an estimated ablated zone based on the determined progress of the ablation procedure.

9. The method according to claim 1, further comprising:
identifying a distal portion of the percutaneous tool in the image data;
determining a line in the image data between the entry point and the distal portion of the percutaneous tool; and
displaying the determined line on the image data.

10. The method according to claim 9, wherein the distal portion of the percutaneous tool is identified based on characteristic data of the percutaneous tool.

11. The method according to claim 9, wherein the distal portion of the percutaneous tool is identified based on an electromagnetic sensor included in the percutaneous tool.

12. The method according to claim 9, wherein identifying the remaining portion of the percutaneous tool includes:
analyzing the image data to identify high intensity areas along the determined line; and
including portions of the high intensity areas along a length of the determined line and within a radius of the determined line, wherein the radius is determined based on a diameter characteristic of the percutaneous tool.

13. The method according to claim 12, wherein identifying the remaining portion of the percutaneous tool further includes excluding portions of the high intensity areas along the length of the determined line and outside of the radius of the determined line.

14. A system for identifying a percutaneous tool in image data, the system comprising:
a percutaneous tool;
a display device; and
a computing device including:
a processor; and
a memory storing instructions which, when executed by the processor, cause the computing device to:
receive image data of at least a portion of a patient's body;
identify an entry point of the percutaneous tool inserted through the patient's skin in the image data;
analyze a portion of the image data including the entry point of the percutaneous tool inserted through that patient's skin to identify a portion of the percutaneous tool in contact with one or more layers of the patient's skin;
determine a trajectory of the percutaneous tool based on the identified portion of the percutaneous tool in contact with the one or more layers of the patient's skin;
identify, in the image data, a remaining portion of the percutaneous tool inserted within the patient's body excluding the portion of the percutaneous tool in contact with the one or more layers of the skin based on the identified entry point and the determined trajectory of the percutaneous tool; and
display the identified portions of the percutaneous tool on the image data.

15. A non-transitory computer-readable storage medium storing a program for identifying a percutaneous tool in image data, the program including instructions which, when executed by a processor, cause a computing device to:
receive image data of at least a portion of a patient's body;
identify an entry point of the percutaneous tool inserted through the patient's skin in the image data;
analyze a portion of the image data including the entry point of the percutaneous tool inserted through that patient's skin to identify a portion of the percutaneous tool in contact with one or more layers of the patient's skin;
determine a trajectory of the percutaneous tool based on the identified portion of the percutaneous tool in contact with the one or more layers of the patient's skin;
identify, in the image data, a remaining portion of the percutaneous tool inserted within the patient's body excluding the portion of the percutaneous tool in contact with the one or more layers of the skin based on the identified entry point and the determined trajectory of the percutaneous tool; and display the identified portions of the percutaneous tool on the image data.

16. The system according to claim 14, wherein the instructions, when executed by the processor, cause the computing device to:

identify a target location in the image data;

determine a path from the entry point to the target location;

determine whether the trajectory of the percutaneous tool corresponds to the path; and display the identified portions of the percutaneous tool, the trajectory, and the path on the image data.

17. The system according to claim 16, wherein if it is determined that the trajectory of the percutaneous tool does not correspond to the path, the instructions, when executed by the processor, cause the computing device to:

determine a difference between the trajectory and the path; and display guidance for adjusting an angle of the percutaneous tool based on the determined difference between the trajectory and the path.

18. The system according to claim 14, wherein the instructions, when executed by the processor, cause the computing device to:

receive configuration settings for an ablation procedure;

identify a position of a radiating portion of the percutaneous tool in the image data;

determine a projected ablation zone based on the configuration settings and the identified position of the radiating portion of the percutaneous tool; and display the projected ablation zone on the image data.

19. The system according to claim 18, wherein the instructions, when executed by the processor, cause the computing device to:

receive an indication that the radiating portion of the percutaneous tool has been activated;

determine a progress of an ablation procedure based on the configuration settings and a time during which the percutaneous tool has been activated; and display an estimated ablated zone based on the determined progress of the ablation procedure.

20. The system according to claim 14, wherein the instructions, when executed by the processor, cause the computing device to:

identify a distal portion of the percutaneous tool in the image data;

determine a line in the image data between the entry point and the distal portion of the percutaneous tool; and display the determined line on the image data.

* * * * *